United States Patent [19]
Akimoto et al.

[11] Patent Number: 5,922,760
[45] Date of Patent: Jul. 13, 1999

[54] AGENT FOR PREVENTION OR ALLEVIATION OF ALLERGY SYMPTOMS

[75] Inventors: Kengo Akimoto, Osaka; Michihiro Sugano; Koji Yamada, both of Fukuoka; Michiko Nonaka, Kasuya-gun; Jiong-Yan Gu, Fukuoka, all of Japan

[73] Assignee: Suntory Limited, Osaka, Japan

[21] Appl. No.: 08/881,822

[22] Filed: Jun. 19, 1997

Related U.S. Application Data

[62] Division of application No. 08/440,337, May 12, 1995, abandoned.

[30] Foreign Application Priority Data

May 12, 1994 [JP] Japan ................................. 6-098798
Apr. 27, 1995 [JP] Japan ................................. 7-104209

[51] Int. Cl.[6] .................... A61K 31/355; A61K 31/34
[52] U.S. Cl. .................... 514/469; 514/458; 514/470; 514/826; 514/853; 514/885
[58] Field of Search ..................... 514/469, 458, 514/470, 826, 853, 885

[56] References Cited

PUBLICATIONS

Chemical Abstracts AN 1990:565418, Yokumoto et al, JP 02138120, Nov. 21, 1988.
Chemical Abstracts AN 1994:686636, Asami et al, JP 06227977, Aug. 16, 1994.

Primary Examiner—Keith D. MacMillan
Attorney, Agent, or Firm—Burns, Doane, Swecker & Mathis, L.L.P.

[57] ABSTRACT

An agent for the prevention or alleviation of allergy symptoms contains as an effective component a dioxabycyclo [3.3.0]octane derivative represented by the following general formula (I):

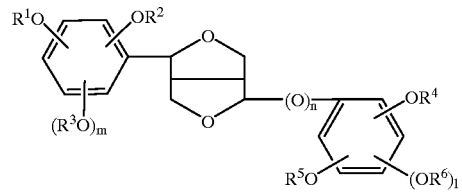

where $R^1$, $R^2$, $R^3$, $R^4$, $R^5$ and $R^6$ each independently represent a hydrogen atom or alkyl group of 1–3 carbon atoms, or $R^1$ and $R^2$ and/or $R^4$ and $R^5$ together represent a methylene or ethylene group, and n, m and l represent 0 or 1.

An agent for the prevention or alleviation of allergy symptoms also contains as an effective component an antioxidant in addition to the dioxabicyclo[3.3.0]octane derivative.

12 Claims, 3 Drawing Sheets

Fig.1

Cont:CONTROL(NO-ADDITION)
Ses:SESAMIN ADDED
Toc:TOCHOPHEROL ADDED
Ses+Toc:SESAMIN AND TOCHOPHEROL ADDED

AGENT FOR PREVENTION OR ALLEVIATION OF ALLERGY SYMPTOMS

This application is a divisional of application Ser. No. 08/440,337, filed May 12, 1995, now abandoned.

BACKGROUND OF INVENTION

1. Field of Invention

The present invention relates to an agent for the prevention or alleviation of allergy symptoms comprising as an effective component a dioxabycyclo[3.3.0]octane derivative, to a food product with an effect of preventing or alleviating allergy symptoms comprising a dioxabycyclo[3.3.0]octane derivative or an extract whose main component is said derivative, and to a method for producing the same.

The present invention also relates to an agent for the prevention or alleviation of allergy symptoms comprising as effective components a dioxabycyclo[3.3.0]octane derivative and an antioxidant, to a food product with an effect of preventing or alleviating allergy symptoms comprising both a dioxabycyclo[3.3.0]octane derivative or an extract whose main component is said derivative and an antioxidant, and to a method for producing the same.

2. Related Art

Allergic asthma, allergic rhinitis, atopic disorders and the like are believed to occur due to interference on biological tissue with the various chemical mediators released from the lungs and other organs, causing contraction of smooth muscle such as bronchial muscle and pulmonary vessels and excessive permeability of epithelial vessels. Of these chemical mediators, the most noted are histamine and SRS-A (slow-reacting release substance of anaphylaxis). In recent years, SRS-A itself has been identified as the peptide leukotrienes $C_4$, $D_4$ and $E_4$ ($LTC_4$, $LTD_4$, $LTE_4$), and the multifarious physiological effects and pathologic connections of these leukotrienes have been widely studied.

Furthermore, SRS-A has been implicated in relation to bronchial asthma, allergic rhinitis and dermatitis, atopic dermatitis, and even ischemic diseases such as myocardial infarction, and cardial anaphylaxis, endotoxic shock, psoriasis, and the like. Consequently, much attention has been directed to the development of agents which suppress production of or act against SRS-A. In addition, with the recent increase in the number of patients with allergy symptoms such as atopic dermatitis and pollenosis, their treatment has become a matter of public concern.

However, at present it is most common to rely on symptomatic therapies, and despite the strong desire for a superior curing agent to thoroughly cure allergy symptoms, it must be said that development thereof is still far out of reach. Recently, a number of different antihistamine drugs and agents which inhibit the production of or act against SRS-A have been developed, but they are still inadequate from the point of view of side effects. Other inhibitors which are used include adrenocorticotropic hormone agents, but these often cause serious side effects in patients and thus should not be widely used as drugs.

SUMMARY OF INVENTION

Consequently, the present invention is aimed at providing a novel agent for the prevention or alleviation of allergy symptoms which has high stability and few side effects, as well as a food product with an effect of preventing or alleviating allergy symptoms and a method of producing the same.

We the present inventors have carried out much research for the purpose of achieving the above-mentioned objects, and as a result have found that dioxabicyclo[3.0.0]octane derivatives isolated from sesame seeds, sesame lees or sesame oil, or obtained by synthesis, are effective for preventing or alleviating allergy symptoms, and that the combined use of the derivatives with antioxidants is also effective for preventing or alleviating allergy symptoms, and the present invention has thus been completed.

That is, the present invention provides agents for the prevention or alleviation of allergy symptoms comprising as an effective component a dioxabycyclo[3.3.0]octane derivative represented by the following general formula (I):

where $R^1$, $R^2$, $R^3$, $R^4$, $R^5$ and $R^6$ each independently represent a hydrogen atom or alkyl group of 1 to 3 carbon atoms, or $R^1$ and $R^2$ and/or $R^4$ and $R^5$ together represent a methylene or ethylene group, and n, m and l represent 0 or 1.

The present invention also provides food products which have an effect of preventing or alleviating allergy symptoms, which are prepared with addition of the above-mentioned derivatives or extracts containing them as main components.

Furthermore, it provides foods with an effect of preventing or alleviating allergy symptoms which are characterized by being prepared with the addition of the above-mentioned derivatives or of extracts containing them as main components, to foods which substantially contain no such derivatives, as well as a method of producing the same.

The present invention further provides agents for the prevention or alleviation of allergy symptoms comprising as effective components an antioxidant in addition to a dioxabicyclo[3.3.0]octane derivative represented by the following general formula (I):

where $R^1$, $R^2$, $R^3$, $R^4$, $R^5$ and $R^6$ each independently represent a hydrogen atom or alkyl group of 1 to 3 carbon atoms, or $R^1$ and $R^2$ and/or $R^4$ and $R^5$ together represent a methylene or ethylene group, and n, m and l represent 0 or 1.

The present invention further provides food products with an effect of preventing or alleviating allergy symptoms, which are prepared with the addition of antioxidants with the above-mentioned dioxabicyclo[3.3.0]octane derivatives or extracts whose main components are those derivatives.

In addition, the present invention provides food products with an effect of preventing or alleviating allergy symptoms, which are characterized by being prepared with the addition of the above-mentioned derivatives or of extracts containing them as main components and of antioxidants, to foods which substantially contain no such derivatives, as well as a method of producing the same.

DETAILED DESCRIPTION

The dioxabicyclo[3.3.0]octane derivatives which are the effective components according to the present invention are compounds represented by the following general formula (I):

where $R^1$, $R^2$, $R^3$, $R^4$, $R^5$ and $R^6$ each independently represent a hydrogen atom or alkyl group of 1 to 3 carbon atoms, or $R^1$ and $R^2$ and/or $R^4$ and $R^5$ together represent a methylene or ethylene group, and n, m and l represent 0 or 1; and here, the alkyl group of 1 to 3 carbon atoms may be methyl, ethyl, n-propyl or isopropyl group, or the like.

More concrete examples of the compounds include sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane and 2-(3,4-methylenedioxyphenyl)-6-(3-methoxy-4-hydroxyphenoxy)-3,7-dioxabicyclo[3.3.0]octane. These compounds may be in the form of glucosides, and enantiomer of the above-mentioned compounds are also within the scope of the present invention.

According to the present invention, the above-mentioned dioxabicyclo[3.3.0]octane derivatives (hereunder, "the derivatives of the present invention") are used alone or two or more thereof are used combination. Furthermore, the derivatives of the present invention are not limited to high purity products, as there may also be used extracts consisting mainly of one or more of the above-mentioned dioxabicyclo [3.3.0]octane derivatives.

An extract containing a derivative of the present invention as a main component may be prepared by extraction by a normal method from a natural substance containing the derivative of the present invention. Natural substances containing derivatives of the present invention include sesame oil, sesame lees, sesame oil byproducts, sesame seeds, Gokahi derived from a medicinal plant which is Acanthopanax gracilistylus W. W. Smith or Acanthopanax sessiliflorus Seem, or Acanthopanax senticosus Harms or Acanthopanax henryi Harms or Acanthopanax verticillatus Hoo; Toboku derived from a medicinal plant which is Paulownia fortunei Hewsl or Paulownia tomentosa; Hakukajuhi derived frow a medicinal plant which is Ginkgo biloba L.; Hihatsu derived from a medicinal plant which is Piper longum L.; Saishin (Asiasari radix) derived from a medicinal plant which is Asarum heterotropoides F. Schm. var. mandshuricum Kitag. or Asarum sieboldii Mig.; etc.

The content of the derivative of the present invention in an extract containing it as a main component is 0.1 wt % or greater, preferably 1.0 wt % or greater, and more preferably 5.0 wt % or greater, and particularly in the case of sesamin and episesamin, the combined content is 0.05 wt % or greater, preferably 0.5 wt % or greater, and more preferably 2.0 wt % or greater.

For example, to obtain an extract consisting mainly of a derivative of the present invention from sesame oil, the extraction and concentration may be done using any of a variety of organic solvents (such as acetone, methyl ethyl ketone, diethyl ketone, methanol, ethanol, etc.) which are substantially immiscible with sesame oil and are able to extract and dissolve the derivative of the present invention.

An example thereof is a method in which sesame oil is uniformly mixed with one of the above-mentioned solvents and then allowed to stand at a low temperature, the phases are separated by a usual method such as centrifugation, and the solvent is then evaporated off from the solvent fraction; more specifically, sesame oil is dissolved in a 2 to 10 fold amount, and preferably a 6 to 8 fold amount of acetone, allowed to stand overnight at $-80°$ C. during which time the oil component precipitates, and acetone is distilled off from the filtrate obtained by filtration to obtain an extract containing a derivative of the present invention as a main component thereof.

Another example is a method in which sesame oil is mixed with hot methanol or hot ethanol and allowed to stand at room temperature, and the solvent is evaporated off from the solvent fraction; more specifically, sesame oil is vigorously mixed in a 2 to 10 fold amount, and preferably a 5 to 7 fold amount of hot methanol ($50°$ C. or higher) or hot ethanol ($50°$ C. or higher), after which the mixture is allowed to stand at room temperature or the phases are separated by a usual method such as centrifugation, and the solvent is distilled off from the solvent fraction to obtain an extract containing a derivative of the present invention as a main component thereof.

In addition, a supercritical gas extract may also be used to obtain an extract containing a derivative of the present invention as a main component thereof.

The sesame oil used may be a purified product or any crude product prior to the decoloring step of the production process for sesame oil.

In order to obtain an extract consisting mainly of a derivative of the present invention from sesame seeds or sesame lees (defatted sesame seeds, residual oil: 8 to 10%), the sesame seeds or sesame lees may be crushed if necessary and then extracted by a usual method using a desired solvent, for example any of the above-mentioned solvents which are used for extraction from sesame oil. After separating off the extract residue, the solvent may be removed from the extract solution by evaporation, etc. to obtain the extract.

The object compound of the derivative of the present invention may be isolated from sesame oil extract, sesame lees extract or sesame seed extract prepared by the methods mentioned above, by treatment according to a usual method such as column chromatography, high performance liquid chromatography, recrystallization, distillation, liquid-liquid exchange distribution chromatography, or the like. More specifically, a derivative of the present invention such as sesamin, episesamin, sesaminol, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane may be obtained by using methanol/water (60:40) in an eluent in a reverse phase column ($5C_{18}$), separating off the above-mentioned extract by high performance liquid chromatography and distilling off the solvent, and then recrystallizing the obtained crystals with ethanol. The methods of obtaining and purifying derivatives of the present invention and extracts containing them as main components are not limited to these.

A derivative of the present invention may also be obtained by synthesis according to a usual method.

For example, sesamin and episesamin may be synthesized by the method of Beroza, et al. [J. Am. Chem. Soc. 78, 1242 (1956)], while pinoresinol (where $R^1=R^4=H$, $R^2=R^5=CH_3$ and n=m=1=0 in the general formula (I)) may be synthesized by the method of Freundenberg, et al. [Chem. Ber., 86, 1157 (1953)] and syringaresinol (where $R^1=R^4=H$, $R^2=R^3=R^5=R^6=CH_3$, n=1 and m=1=1 in the general formula (I)) may be synthesized by the method of Freundenberg, et al. [Chem. Ber., 88, 16(1955)].

The derivatives of the present invention or extracts containing them as main components may also be combined with antioxidants for use as effective components according to the present invention. The antioxidants available for use include natural antioxidants such as tocopherols, flavone derivatives, phyllodulcins, kojic acid, gallic acid derivatives, catechins, fukinolic acid, gossypol, pyrazine derivatives, sesamol, guaiacol, guaiac resin, p-coumalic acid, nordihydroguaiaretic acid, sterols, terpenes, nucleic acid bases, carotenoids, etc. and synthetic antioxidants such as butylhydroxyanisole (BHA), butylhydroxytoluene (BHT), monotertiary-butylhydroquinone (TBHQ), 4-hydroxymethyl-2,6-ditertiarybutylphenol (HMBP), etc.

Tocopherols are particularly preferred from among these antioxidants, and examples of tocopherols include α-tocopherol, β-tocopherol, γ-tocopherol, δ-tocopherol, ε-tocopherol, ξ-tocopherol, η-tocopherol and tocopherol esters (tocopherol acetate, etc.). In addition, as carotenoids there may be mentioned β-carotene, canthaxanthin, astaxanthin, etc.

There are no particular restrictions on the proportions of the derivative of the present invention and the antioxidant in combination, but the antioxidant is preferably present at between 0.001 parts by weight and 1000 parts by weight with respect to 1 part by weight of the derivative of the present invention. A more preferred range is from 0.01 to 100 parts by weight, and an even more preferred range is from 0.029 to 40 parts by weight with respect to 1 part by weight of the derivative of the present invention.

The effective components of the present invention, namely the derivatives of the present invention alone or in combination with the antioxidants, is effective for the prevention or alleviation of allergy symptoms because they suppress the release of chemical mediators (histamine, $LTB_4$, $LTC_4$, etc.) by causing an increase of the levels of IgA which inhibits allergen absorption and of IgG which arrests reaction between allergens and IgE. Among the allergy symptoms which are the object of the present invention there may be mentioned symptoms of allergic diseases such as atopic dermatitis, adolescent atopic dermatitis, hives, contact dermatitis, senile dermatosis, bronchial asthma, allergic rhinitis, pollenosis, ischemic diseases, cardial anaphylaxis, endotoxic shock, psoriasis, drug allergy, food allergy, insect allergy, and the like. According to the present invention, the alleviation of symptoms has a wide meaning, also including curing of the disorder.

For example, in the case of pollenosis, the effective components of the present invention, particularly the derivative of the present invention and the antioxidant, would be expected to bind to IgG distributed throughout the mucous membrane before pollen (allergens) absorbed at the surface of the nasal mucosa react with IgE attached to mast cells, thus inhibiting the reaction between the allergen and the IgE, and therefore no histamine is released from the mast cells and the allergy symptoms are suppressed.

Food allergies are allergies provoked by daily ingested foods, causing in addition to symptoms in the digestive organs where the food first contacts (swelling of oral mucous membrane, itching sensation, irritability, vomiting, abdominal pain, diarrhea), also cutaneous symptoms (eczema, hives), respiratory symptoms (nasal allergy, bronchial asthma), urinary symptoms (increased urination frequency, nocturnal urination), nervous symptoms (migraine), and the like. Such allergens include eggs, milk, soybeans, peanuts, chocolate, wheat flour, marine products, spices, preservatives, coloring agents and other food additives, microorganisms, medicines, and the like. With bronchial asthmatic children there is first an outbreak of eczema due to food allergy, from which nasal allergy due to inhaled allergens then progresses to bronchial asthma. Most important for avoiding outbreak of such food allergies is to avoid intake of the allergens, but this is not practical.

Use of the effective components of the present invention, particularly the derivatives of the present invention and the antioxidants, is also believed to exhibit an anti-allergic effect by causing an increase in the level of IgA antibody produced by the mesenteric lymph node, allowing it to adhere to the food (allergen) absorbed at the enteric mucosa.

When the effective components of the present invention are used as drug products, their form of administration may be either oral or parenteral depending on convenience, such forms including injections, infusions, powders, granules, tablets, capsules, enteric coated tablets, lozenges enteric capsules, troche, mixture for internal use, suspensions, emulsions, syrups, liquid for external use, tomentations, nasal drops, ear drops, eye drops, inhalants, ointments, lotions, suppositories, etc. which may be used either alone or in combination depending on the symptoms.

These preparations may be prepared according to usual methods using, together with the active components, known adjuvants which are normally used in the field of drug preparation, including excipients, binders, preservatives, stabilizers, disintegrators, lubricants, flavor correctors, and the like, depending on the purpose. For example, when preparing injections, drug solubilizers such as non-ionic surfactants and the like may be used, and more specifically, a derivative of the present invention may be heated to dissolution in a non-ionic surfactant such as an 80-fold volume of POE (60) hydrogenated castor oil or POE sorbitan monooleate, with dilution with physiological saline to complete the preparation. Alternatively, appropriate isotonizing agents, stabilizers, preservatives and soothing agents may also be added if necessary.

In addition, external preparations may employ vaseline, paraffin, fats and oils, lanolin, macrogol, etc. as bases to prepare ointments, creams and the like by common methods. Also, the dosages will differ depending on the purpose of administration and conditions of the patient (sex, age, body weight, etc.), but normally for administration to adults, the total amount of the derivative of the present invention may be appropriately adjusted in the range of 1 mg to 10 g per day, preferably 1 mg to 2 g per day, and more preferably 1 mg to 200 mg per day in the case of oral administration, and in the range of 0.1 mg to 1 g per day, preferably 0.1 mg to 200 mg per day, and more preferably 0.1 mg to 100 mg per day in the case of parenteral administration.

Furthermore, when the derivatives of the present invention are administered together with antioxidants, especially tocopherols, the dosages of the derivatives of the present invention will differ depending on the purpose of administration and conditions of the patient (sex, age, body weight, etc.), but normally for administration to adults, the total amount of the derivative of the present invention may be appropriately adjusted in the range of 0.1 mg to 2 g per day, preferably 0.1 mg to 500 mg per day, and more preferably 0.1 mg to 100 mg per day in the case of oral administration, and in the range of 0.01 mg to 200 mg per day, preferably 0.01 mg to 50 mg per day, and more preferably 0.01 mg to 20 mg per day in the case of parenteral administration, while the mixing ratio of the derivative of the present invention and the antioxidant may be appropriately adjusted in the range of 0.001 to 1000 parts by weight, preferably 0.01 to 100 parts by weight, and more preferably 0.029 to 40 parts by weight of the antioxidant to 1 part by weight of the derivative of the present invention. The use of the derivatives of the present invention with antioxidants, particularly tocopherols, is expected to provide a synergistic effect of prevention and alleviation of allergy symptoms.

The derivatives of the present invention are clearly superior from the point of view of safety, since they are compounds discovered from traditional foods, or related compounds. This is also clear from the fact that when sesamin was continuously administered (orally) to 7-week-old male IRC mice at 2.14 g/day/kg for 2 weeks, no abnormal symptoms were observed.

When the effective components of the present invention or are used as food products, they may be in the form of the above-mentioned drug preparations, or in the form of solid or liquid foods and popular foods, including as bread, noodles, rice confectioneries (such as biscuits, cake, candy, chocolate, Japanese sweets); agricultural foods such as tofu and their processed products; fermented foods such as Japanese sake, medicinal alcoholic drinks, sweet sake (mirin), vinegar, soysauce and soypaste (miso); oil and fat foods such as dressings, mayonnaise, margarine, shortening and edible fat and oil; livestock food products such as yogurt, ham, bacon and sausage; marine foods such as steamed fish paste (kamaboko), boiled fish paste (hanpen), and fried fish paste; and beverages such as juices, soft drinks, sports drinks, alcoholic drinks, tea and the like.

Also, when used as health foods or functional foods, they may be in the form of the above-mentioned drug preparations or food products, but they may also be in processed form, such as liquid foods, semi-digested nutrient foods, component nutrient foods or drinks to which have been added, for example, proteins (proteins from protein sources such as milk protein, soybean protein and egg albumin which have balanced amino acids and high nutritional value are most widely used, but decomposition products of these, egg-white oligopeptides, soybean hydrolysates, etc. and mixtures of amino acid monomers may also be used), saccharides, fats, trace elements, vitamins, emulsifiers or spices.

A food product of the present invention may be processed by a common method of production with addition of a prescribed amount of a derivative of the present invention or an extract which contains it as a main component, to a food which substantially contains no derivative of the present invention. The mixing amount thereof will depend on the form of the preparation or food and is not particularly restricted, but generally it is preferred to be from 0.001 to 50%. Also, it may be taken as a health food or functional food product for the prevention or alleviation of the above-mentioned allergy symptoms, and for the preparation of hospital food, a derivative of the present invention or an extract which contains it as a main component may be added to a desired food which substantially contains no derivative of the present invention, and given to a patient in the form of a functional food product prepared on the spot, under the control by a direction according to doctors diet prescription.

According to the present invention, a food substantially containing no derivative of the present invention is a food which is not prepared from a starting material such as sesame, but foods prepared from sesame and the like are also included as foods substantially containing no derivatives of the present invention if the food products in their final form contain only a trace amount of a derivative of the present invention, with the content of the derivative of the present invention being less than 0.1 mg, and preferably 0.8 mg or less per daily portion of the food; or the total content of sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane being less than 0.1 mg, and preferably 0.8 mg or less per daily portion of the food.

The food products of the present invention are preferably taken orally at a total daily dosage of derivatives of the present invention in the range of 1 mg to 10 g, preferably 1 mg to 2 g, and more preferably 1 mg to 200 mg as a rule, for the purpose of prevention or alleviation of allergy symptoms and health maintenance.

In addition, when a derivative of the present invention or an extract containing it as a main component is taken together with an antioxidant, particularly a tocopherol, as a rule, it is preferably taken orally, with the total daily dosage of the derivative of the present invention being in the range of 0.1 mg to 2 g, preferably 0.1 mg to 500 mg, and more preferably 0.1 mg to 100 mg, and the mixing ratio of the derivative of the present invention and the antioxidant being in the range of 0.001 to 1000 parts by weight, preferably 0.01 to 100 parts by weight, and more preferably 0.029 to 40 parts by weight of the antioxidant to 1 part by weight of the derivative of the present invention. The combined use of a derivative of the present invention and an antioxidant, particularly a tocopherol, is expected to provide a synergistic effect of prevention and alleviation of allergy symptoms and health maintenance.

In cases where a derivative of the present invention or an extract containing it as a main component is added to a food which substantially contains no derivative of the present invention but contains an antioxidant, particularly a tocopherol, the derivative of the present invention or the extract containing it as a main component may be added so that the proportion of the derivative of the present invention and the antioxidant in the food product in its final form is in the range of 0.001 to 1000 parts by weight, preferably 0.01 to 100 parts by weight, and more preferably 0.029 to 40 parts by weight of the antioxidant to 1 part by weight of the derivative of the present invention. An antioxidant may be further added at this time, if necessary.

The present invention is more concretely described below with reference to the following examples.

EXAMPLES

Example 1

Experimental Animals and Diets

Four groups of 4-week-old (average body weight: 96 g) male Brown-Norway (BN) rats (from Seiwa Experimental Animals) were formed with 8 rats per group. One group was given normal diet comprising 20% casein, 5% corn oil, 5% cellulose, 3.5% mineral mixture (AIN-TX: American Institute of Nutrition), 1% vitamin mixture (AIN-TX), 0.2% choline bitartrate, 0.3% DL-methionine, 15% corn starch and 50% sucrose. The remaining 3 groups were given diet containing 0.5% sesamin or 0.5% α-tocopherol at the expense of sucrose, with further addition of 0.5% sesamin and 0.5% α-tocopherol at the expense of sucrose. The sesamin used was a mixture of sesamin and episesamin (sesamin: 55.2%, episesamin: 44.4%, purity: 99.6%) purified by the method described in Japanese Unexamined Patent Publication No. 3-27319. After 3 weeks of feeding, blood was taken from the abdominal aorta under diethyl ether anesthesia, and the lung and spleen were excised.

Extraction and Measurement of Leukotriene $C_4$

The leukotriene $C_4$ ($LTC_4$) concentration in the lung tissue excised from the rats was assayed by radioimmunoassay according to a common method.

Figure 1:
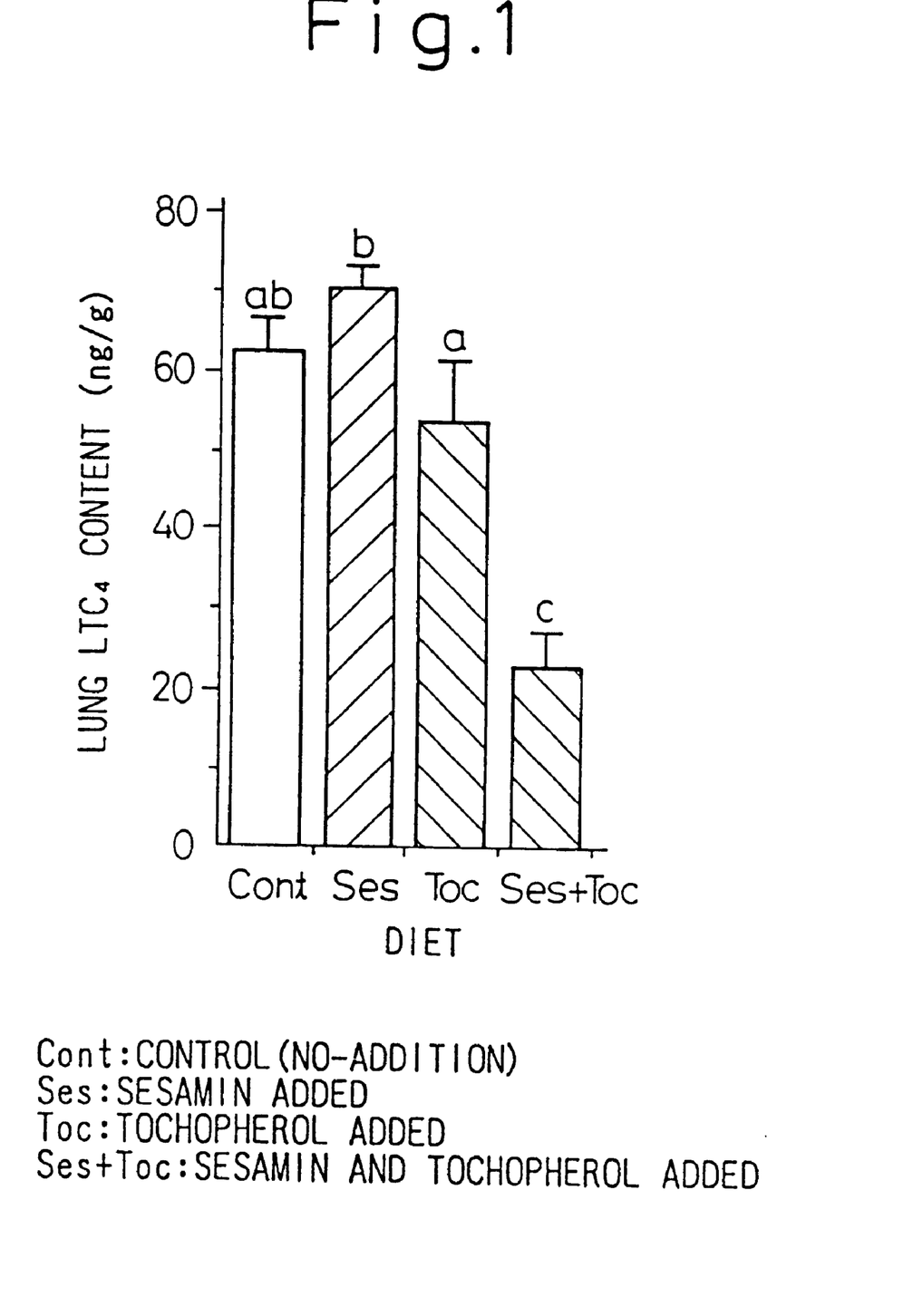
FIG. 1 is a graph showing the difference in lung tissue $LTC_4$ concentrations of male BN rats given diets containing sesamin and/or tocopherol.

The results are shown in FIG. 1. As this graph clearly shows, $LTC_4$ was significantly lower with administration of both sesamin and tocopherol.

Analysis of $CD4^+$ (%), $CD8^+$ (%) by Flow Cytometry

The proportions of $CD4^+$ and $CD8^+$ cells in the blood were measured by flow cytometry (FCM). The spleens excised from the rats were transferred to 5 ml dishes containing RPMI 1640 medium, the fat was removed from the spleens, both ends were cut off, and the remaining portions were cut into 3 or 4 pieces. These were transferred to dishes containing fresh RPMI 1640 medium and triturated with a glass slide, and cells including lymphocytes were collected.

A 4 ml portion of lymphocyte separating medium (LSM) was added to each group of cells and the mixtures centrifuged, and then the resulting lymphocyte layers were drawn out for separation and transferred to RPMI 1640 medium. To each of the cell suspensions there was added 10 ml of fetal bovine serum (FBS), and dilution was performed with this medium to prepare solutions of $1 \times 10^6$ cells/ml, which were poured into 10 ml dishes. To each 10 ml dish there was added 100 μl of lysine solution at increasing final concentrations of from $1 \times 10^{-4}$ ng/ml to 10 ng/ml.

After 48 hours, a portion of each culture solution was taken for antibody measurement, and the remaining cell suspension was adequately pipetted and then transferred to a centrifuge tube containing 10 ml of RPMI 1640 medium and centrifuged at 1200 rpm for 5 minutes. Each of the supernatants was discarded, 1.5 ml of RPMI 1640 was again added and the mixtures thoroughly pipetted, and 100 μl thereof was poured into microtubes.

After centrifugation the supernatants were discarded, 2 ml of RPMI 1640 medium was added to the precipitated lymphocytes, and the mixtures were thoroughly pipetted, 1 ml each, into microtubes, and again centrifuged at 1200 rpm for 5 minutes. The supernatants were discarded, 100 μl of 10% inactivated FBS-containing PBS (phosphate buffered saline) was added, 5 μl each of anti-rat $CD_4$-FITC-labelled antibody and anti-rat $CD_8$-PE-labelled antibody were added, and the mixtures were allowed to stand on ice for 30 minutes (stirring every 10 minutes). In addition, 1 ml of 10% inactivated FBS/PBS was added, the mixtures were centrifuged at 1200 rpm for 5 minutes, the supernatants were again discarded, and the same procedure was repeated. The supernatants were discarded, 0.5 ml each of 4% paraformaldehyde solution and PBS were added and the mixtures were thoroughly pipetted (immobilization of lymphocytes). These procedures were performed for the lymphocytes at all of the concentrations of lysine. The following day, the immobilized lymphocytes were measured by flow cytometry (FCM) to determine the proportions of $CD4^+$ cells and $CD8^+$ cells. The results are shown in Table 1.

TABLE 1

| Group | Cont. | Ses | Toc | Ses + Toc |
|---|---|---|---|---|
| $CD4^+$ | $41.1 \pm 3.3^a$ | $33.4 \pm 1.7^b$ | $32.6 \pm 1.6^b$ | $37.9 \pm 2.0^{ab}$ |
| $CD8^+$ | $9.6 \pm 0.6^a$ | $7.4 \pm 0.5^b$ | $7.1 \pm 0.5^b$ | $7.3 \pm 0.2^b$ |
| $CD4^+/CD8^+$ | $4.3 \pm 0.1^a$ | $4.6 \pm 0.2^a$ | $4.6 \pm 0.4^a$ | $5.2 \pm 0.4^a$ |

Values: average ± SE
Cont.: Control (no addition)
Ses: 0.5% sesamin-added
Toc: 0.5% tocopherol-added
Ses ± Toc: 0.5% sesamin and 0.5% tocopherol-added
Significant differences between different letters, a and b: $P < 0.05$
$CD4^+$: Helper T cell
$CD8^+$: Suppressor T cell As is clear from Table 1, the spleen lymphocyte helper T cell ($CD4^+$) with an iinmunoreactive effect was significantly lower with addition of sesamin.

Measurement of Serum IgM, IgA, IgG and IgE Concentrations by ELISA (Enzyme-linked Immunosorbent Assay)

The above-mentioned blood taken from rat abdominal aorta was used.

The reagents used were 50 mM carbonate-buffered rinsing solution (0.05% Tween 20/PBS, Wako Pure Chemical Industry), a blocking agent (Yukijirushi Dairy), 0.2 M citrate buffer containing primary and secondary IgA, IgM and IgG (Mie Kagaku), ABTS solution, substrate solution, reaction suspending solution, etc. The primary antibodies of IgM, IgA and IgG were diluted 1000-fold with 50 mM carbonate buffer (pH 9.6), poured into a 96-well plate at 100 μl in each well, and allowed to stand at 37° C. for 1 hour.

After the plate was rinsed 3 or 4 times with rinsing solution, 300 μL of 4-fold diluted Block Ace was poured into each well and allowed to stand at 37° C. for 1 hour for blocking. After rinsing the plate 3 or 4 times with rinsing solution, 50 μl of culture supernatant containing IgM, IgA and IgG was added to each well and allowed to stand at 37° C. for 1 hour for reaction. After rinsing the plate 3 or 4 times with rinsing solution, the enzyme-labelled anti-IgM, IgA and IgG secondary antibodies were poured into the 96-well plate at 100 μL per well and allowed to stand at 37° C. for 1 hour.

The plate was further rinsed 3 or 4 times with rinsing solution, and then the substrate solution was added to the 96-well plate at 100 μL per well, and after reaction at 37° C. for 5–15 minutes, the reaction suspending solution was added at 100 μL per well, and an ELISA microplate spectrophotometer was used to measure the absorbance of each well at 415 nm. IgM, IgA and IgG standard solutions were added to the corresponding IgM, IgA and IgG culture supernatants, and the amounts of IgM, IgA and IgG in each culture supernatant were assayed from their primary regression lines.

The method of measuring the IgE concentration was almost the same as the method described above for measuring the IgM, IgA and IgG antibody concentrations, except that the abidin-biotin method was used in which enzyme-labelled abidin is added after 100 μL of biotin-labelled anti-IgE antibody is poured into each well of the plate. The plate was allowed to stand at 37° C. for 30 minutes. After rinsing 3 or 4 times, the substrate solution and reaction suspending solution were each added, and the IgE content was measured in the same manner as described above.

Figure 2:
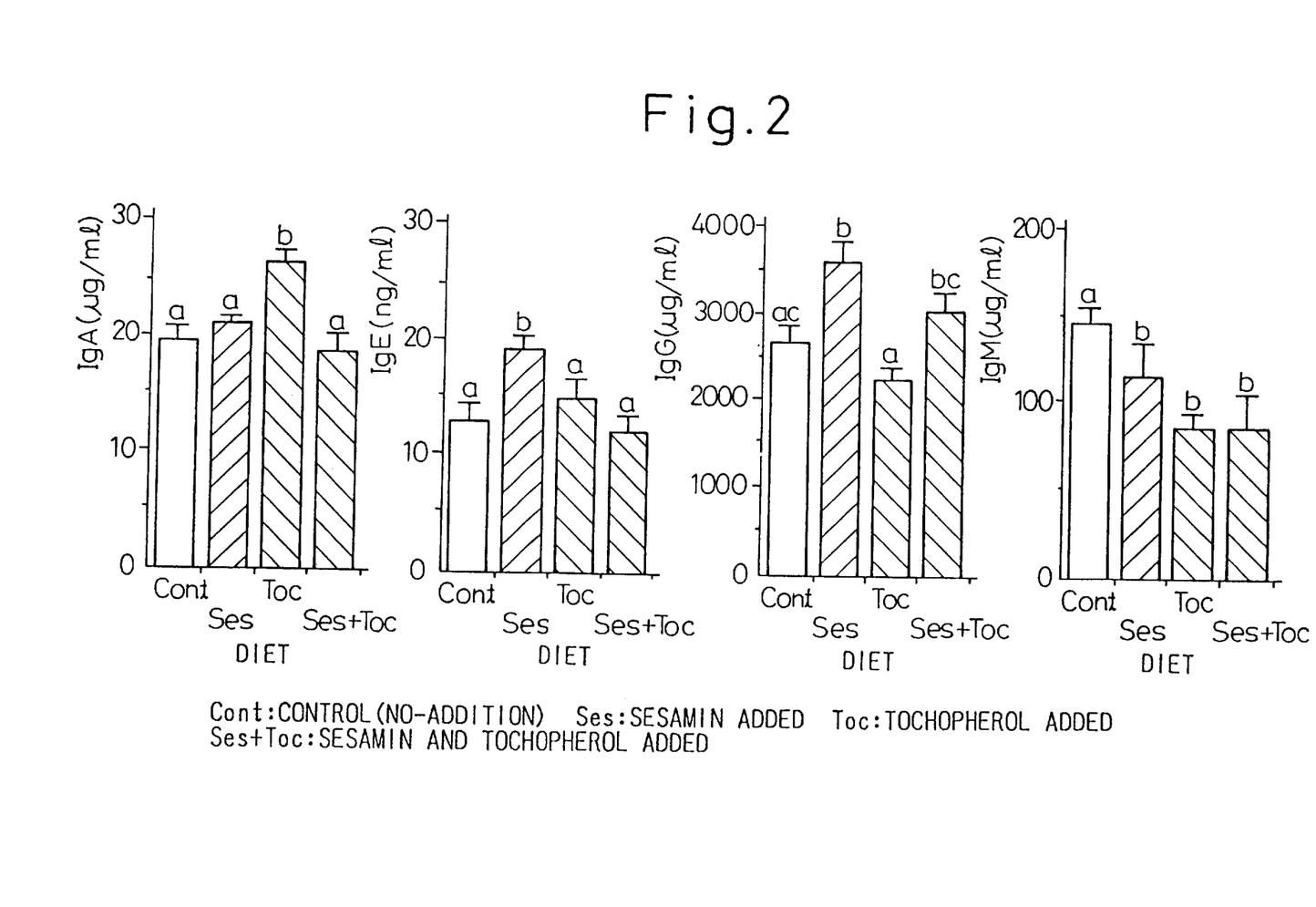
FIG. 2 is a group of graphs showing the serum immunoglobulin IgA, IgE, IgG and IgM concentrations of male BN rats given diets containing sesamin and/or tocopherol.

The results are shown in FIG. 2. In the group given α-tocopherol (α-Toc), the level of the allergen absorption-inhibiting factor IgA was significantly higher, while in the group given sesamin and α-tocopherol (Ses+α-Toc), the level of IgE, which plays a major role in Type I allergy, was significantly lower. These results suggest that the combined use of sesamin and α-tocopherol has an anti-allergic action.

Discussion

The production of the allergy-causing chemical mediator LTC4 was lower in the α-Toc group and Ses+α-Toc group, but was higher in the sesamin (Ses) group. Also, regarding the production of another allergy-causing chemical mediator PGE2, a tendency toward reduction was observed in the Ses and α-Toc groups, but there was an increase in the Ses+α-Toc group. These results show that sesamin and α-tocopherol have different action sites, but both have suppressing effects against allergic reactions. In addition, it was confirmed that simultaneous administration of sesamin and α-tocopherol results in a synergistic effect of the two. It is indicated that the effective components of the present invention, sesamin or sesamin and α-tocopherol, do not act at a single site of immunoreactions, but rather control immunoreactions by controlling more than one reaction. The use of such a combination of allergy-suppressing factors is believed to attenuate allergic responses in allergy patients, and prevent progression of healthy persons to allergic constitutions.

Example 2

Six groups of 4-week-old (average body weight: 96 g) male Brown-Norway (BN) rats were formed with 8 rats per group. One group was given normal diet comprising 20% casein, 5% corn oil, 5% cellulose, 3.5% mineral mixture (AIN-TM), 1% vitamin mixture (AIN-TM), 0.2% choline bitartrate, 0.3% DL-methionine, 15% corn starch and 50% sucrose. The remaining 5 groups were given diets respectively containing, at the expense of sucrose, 0.5% sesaminol prepared from crude sesame oil (compound A), sesamolin prepared from crude/purified sesame oil (compound B), or 2-(3,4-methylenedioxyphenyl)-6-(3-methoxy-4-hydroxyphenyl)-3,7-dioxabicyclo[3.3.0]octane (compound C), 2,6-bis-(3-methoxy-4-hydroxyphenyl)-3,7-dioxabicyclo[3.3.0]octane (compound D) or 2-(3,4-methylenedioxyphenyl)-6-(3-methoxy-4-hydroxyphenoxy)-3,7-dioxabicyclo[3.3.0]octane (compound E) prepared by acetone extraction of sesame seeds, the preparation being according to a method present under patent application (Japanese Unexamined Patent Publication No. 1-243992), with further addition of 0.5% α-tocopherol. After 3 weeks, the leukotriene $C_4$ ($LTC_4$) concentrations in the lung were examined according to Example 1. $LTC_4$ production in the lung in the normal diet group was 62.7 ±3.9 (ng/g), whereas in the groups given diet containing compounds A, B, C, D and E with α-tocopherol, it was significantly lower at 32.1 ±4.6, 34.4 ±5.4, 40.2 ±3.8, 44.5 ±3.4 and 39.7 ±4.7, respectively.

Example 3

Experimental Animals and Diets

Four groups of 4-week-old male (average body weight: 147 g) Sprague-Dawley (SD) rats (Seiwa Experimental Animals) were formed with 6 rats per group. One group was given normal diet comprising 20% casein, 5% corn oil, 5% cellulose, 3.5% mineral mixture (AIN-TX: American Institute of Nutrition), 1% vitamin mixture (AIN-TM), 0.2% choline bitartrate, 0.3% DL-methionine, 15% corn starch and 50% sucrose. The remaining 3 groups were given diets containing 0.5% sesamin or 0.5% α-tocopherol at the expense of sucrose, with further addition of 0.5% sesamin and 0.5% α-tocopherol at the expense of sucrose. The sesamin used was the same as used in Example 1. After 3 weeks of feeding, blood was taken from the abdominal aorta under diethyl ether anesthesia, and the lung and spleen were excised.

The leukotriene $B_4$ ($LTB_4$) and leukotriene $C_4$ ($LTC_4$) concentrations in the lung and spleen tissues excised from the rats were assayed by radioimmunoassay according to a usual method. In addition, 1.5 ml of plasma was placed in a centrifuge tube containing 1 ml of 1 N $HClO_4$ and mixed therewith, and then centrifuged (3000 rpm, 30 minutes), and the histamine was extracted and assayed according to a usual method.

Figure 3:
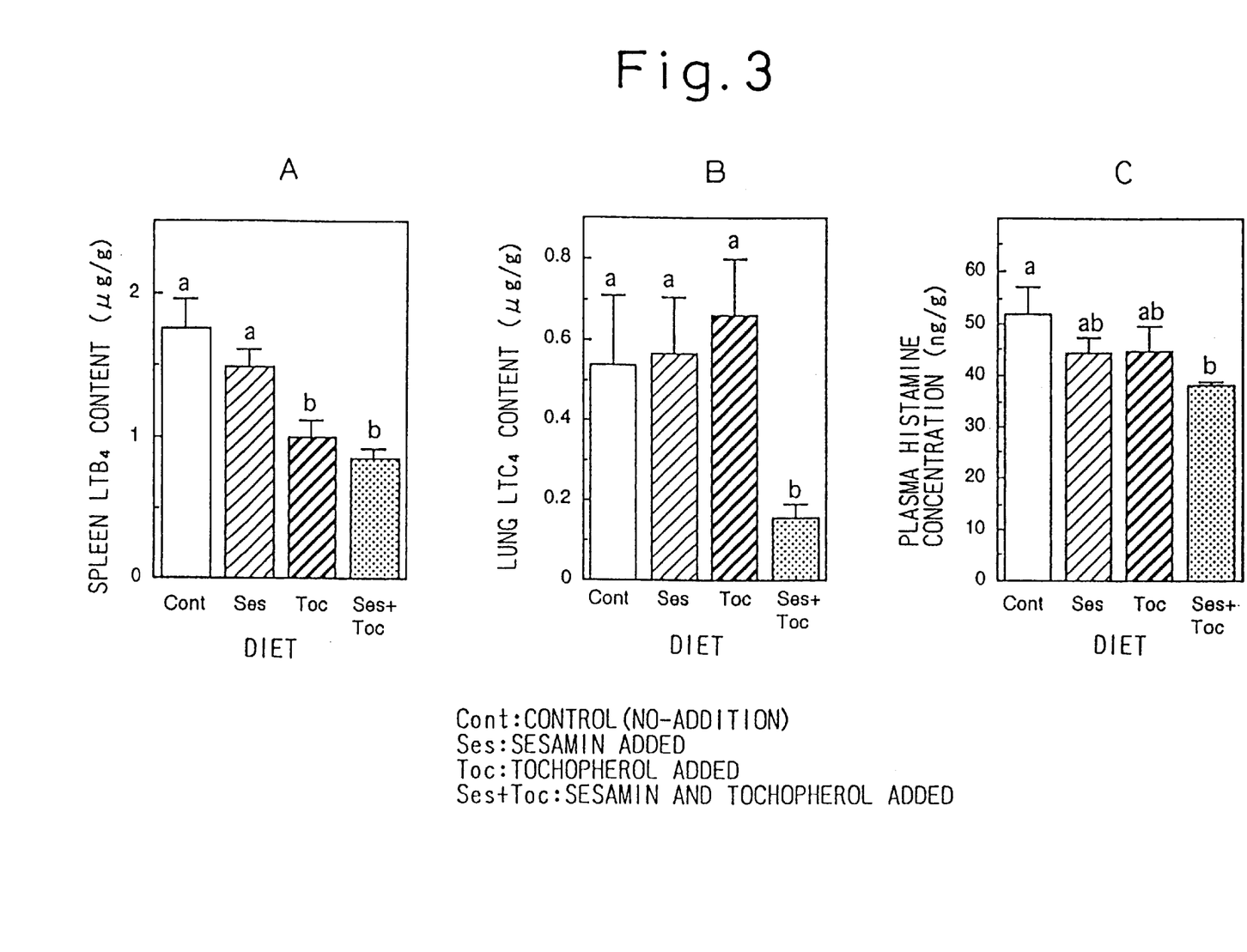
FIG. 3 is a group of graphs showing the differences in spleen tissue $LTB_4$ concentrations, lung tissue $LTC_4$ concentrations and blood plasma histamine concentrations of male SD rats given diets containing sesamin and/or tocopherol.

The results are shown in FIG. 3. As is clear from these graphs, the leukotriene $B_4$ ($LTB_4$) concentration in the spleen tissue and the histamine concentration in the plasma were lower with administration of sesamin and tocopherol, and were even more significantly lower with administration of both. In addition, the leukotriene $C_4$ ($LTC_4$) concentration in the lung tissue was significantly lower in a synergistic manner by administration of both sesamin and tocopherol. Thus, there were significantly lower levels of allergy-related chemical mediators with administration of sesamin alone or a combination of sesamin and tocopherol.

For measurement of the mesenteric lymph node immunoglobulin concentration, mesenteric lymph node was excised and the lymphocytes were squeezed out into RPMI 1640 medium (Nissui Pharmaceutical Co.), and after incubating the cells at 37° C. for 30 minutes to remove the fibroblasts, 5 ml of the cell suspension was layered on 4 ml of Lympholyte-Rat (Cedarlane, Canada) and centrifuged (1500×g, 30 min). The lymphocyte band at the interface was recovered, and the cells were rinsed three times with the RPMI 1640 medium. The lymphocytes were cultured in a 10% fetal bovine serum (FBS, Intergen Co., U.S.A.)/RPMI 1640 medium. The MLN lymphocytes were adjusted to $2\times10^6$ cells/ml and incubated at 37° C. for 6 hours, after which the concentrations of IgE, IgA, IgM and IgG were measured by the enzyme-linked immunosorbent assay (ELISA).

The results are shown in Table 2. The concentration of the anti-allergic IgA was significantly higher with administration of sesamin. Furthermore, The concentration of IgG which inhibits reaction between allergens and IgE antibody was significantly higher in a synergistic manner with administration of both sesamin and tocopherol.

As shown above, sesamin alone or a combination of sesamin and tocopherol may be used to prevent or improve allergy symptoms.

TABLE 2

Influence of sesamin and tocopherol on immunoglobulin concentration in mesenteric lymph node lymphocytes

| Group | Concentration (ng/g) | | | |
|---|---|---|---|---|
| | IgA | IgG | IgM | IgE |
| Control (no addition) | 27.4 ± 1.3[a] | 4.7 ± 0.3[a] | 0.7 ± 0.3[a] | 1.9 ± 1.1 |
| Sesamin-added | 61.8 ± 3.1[b] | 4.6 ± 0.2[a] | n.d. | 0.2 ± 0.1 |
| Tocopherol-added | 30.1 ± 1.0[a] | 7.3 ± 0.9[b] | 1.7 ± 0.5[a] | 0.5 ± 0.2 |
| Sesamin- and tocopherol-added | 46.9 ± 0.8[c] | 14.8 ± 0.8[c] | 4.1 ± 0.6[b] | 1.7 ± 0.4 |

Values: Average ±SE
Significant differences between different letters, a, b and c: $P < 0.05$
n.d.: Not detected

Example 4

To 100 g of butter fat from which the buttermilk had been removed by the stirring operation (churning) during the butter manufacturing process, there were added 1.2 g of a mixture of sesamin and episesamin (sesamin: 51.3%, episesamin: 47.8%) and 1.2 g of tocopherol acetate, and the kneading operation (working) was carried out to a homogeneous composition to obtain butter containing effective components of the present invention, which had an effect of preventing or improving allergy symptoms.

Example 5

A 0.5 g portion of the effective components of the present invention was mixed with 20.5 g of silicic anhydride, and then 79 g of corn starch was added prior to further mixing. A 100 ml portion of a 10% hydroxypropylcellulose/ethanol solution was added to the mixture which was then heated, extruded and dried by usual methods to obtain granules.

Example 6

A 20 g portion of silicic anhydride was mixed with 3.5 g of a mixture of sesamin and episesamin (sesamin: 51.3%, episesamin: 47.8%) and 0.5 g of tocopherol acetate, and then 10 g of microcrystalline cellulose, 3.0 g of magnesium stearate and 60 g of lactose were added and mixed therewith, and the mixture was tabletted using a single-shot slug tabletting machine to make tablets with a diameter of 7 mm and a weight of 100 mg.

Example 7

A 2.5 g portion of the effective components of the present invention was dissolved at 122° C. in 200 g of the non-ionic surfactant TO-10M (Nikko Chemicals), and 4.7975 liters of physiological saline sterilized by heating at 60° C. was added and thoroughly mixed therewith, after which the mixture was distributed into aseptic vials which were sealed to prepare injections.

Example 8

Water was added to 100 parts by weight of gelatin and 35 parts by weight of glycerine food additive, which were dissolved therein at 50 to 60° C. to prepare a gelatin membrane with a viscosity of 20,000 cps. Then, 95.1% wheat germ oil, 2.9% vitamin E oil and 2% sesamin were mixed to prepare the contents. These were used for capsule molding and drying by usual methods, to prepare soft capsules containing 180 mg of the contents per capsule. Each capsule contained 3.6 mg of sesamin and 2.34 mg of α-tocopherol.

Clinical Example 1

Atopic dermatitis patients (5) were orally administered one of the tablets prepared in Example 6 three times a day at morning, noon and night (total per tablet dosage of dioxabicyclo[3.3.0]octane derivative and antioxidant: 12.4 mg) for a period of 8 weeks, and the efficacy thereof was evaluated. As a result, in 3 of the atopic dermatitis patients, the present invention was judged to be somewhat effective, effective or very effective.

Clinical Example 2

Atopic rhinitis patients (5) were orally administered one of the capsules prepared in Example 8 three times a day at morning, noon and night (total per capsule dosage of dioxabicyclo[3.3.0]octane derivative and antioxidant: 17.82 mg) for a period of 8 weeks, and the efficacy thereof was evaluated. As a result, in 3 of the atopic rhinitis patients, the present invention was judged to be somewhat effective, effective or very effective.

Clinical Example 3

Pollenosis patients (5) were orally administered one of the capsules prepared in Example 8 three times a day at morning, noon and night (total per capsule dosage of dioxabicyclo[3.3.0]octane derivative and antioxidant: 17.82 mg) for a period of 8 weeks, and the efficacy thereof was evaluated. As a result, in 2 of the pollenosis patients, the present invention was judged to be somewhat effective, effective or very effective.

We claim:

1. A method for the prevention or alleviation of allergy symptoms, comprising administering to a person in need of such prevention or alleviation, an effective amount to prevent or alleviate allergy symptoms of a dioxabicyclo[3.3.0] octane derivative represented by the following general formula (I):

wherein $R^1$, $R^2$, $R^3$, $R^4$, $R^5$ and $R^6$ each independently represent a hydrogen atom or alkyl group of 1–3 carbon atoms, or $R^1$ and $R^2$, and/or $R^4$ and $R^5$ together represent a methylene or ethylene group, and n, m and l represent 0 or 1, and an antioxidant.

2. The method for the prevention or alleviation of allergy symptoms according to claim 1, wherein the compound of the formula (I) and the antioxidant are administered in the form of a food or drink.

3. The method for the prevention or alleviation of allergy symptoms according to claim 2, wherein said food or drink is a health food or functional food.

4. The method for the prevention or alleviation of allergy symptoms according to claim 1, wherein said antioxidant is tocopherol.

5. The method for the prevention or alleviation of allergy symptoms according to claim 2, wherein said antioxidant is tocopherol.

6. The method for the prevention or alleviation of allergy symptoms according to claim 1, wherein said dioxabicyclo[3.3.0]octane derivative administered is at least one of sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane.

7. The method for the prevention or alleviation of allergy symptoms according to claim 3, wherein said dioxabicyclo[3.3.0]octane derivative administered is at least one of sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane.

8. The method for the prevention or alleviation of allergy symptoms according to claim 6, wherein said dioxabicyclo[3.3.0]octane derivative administered is at least one of sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane.

9. The method for the prevention or alleviation of allergy symptoms according to claim 1, wherein the allergy symptoms prevented or alleviated are selected from the group consisting of atopic dermatitis, adolescent atopic dermatitis, hives, contact dermatitis, senile dermatosis, bronchial asthma, allergic rhinitis, pollenosis, ischemic diseases, cardia anaphylaxis, endotoxic shock and psoriasis.

10. The method for the prevention or alleviation of allergy symptoms according to claim 1, wherein the allergy symptoms are associated with an allergy selected from the group consisting of drug allergy, food allergy and insect allergy.

11. The method for the prevention or alleviation of allergy symptoms according to claim 10, wherein the allergy symptoms are associated with a food allergy.

12. The method for the prevention or alleviation of allergy symptoms according to claim 1, wherein the dioxadicyclo[3.3.0]octane derivative and the antioxidant are administered orally or parentally to a person in need of such prevention or alleviation.

* * * * *